United States Patent
Tao et al.

(10) Patent No.: US 12,232,871 B2
(45) Date of Patent: Feb. 25, 2025

(54) MULTI-SPECTRAL FUNDUS IMAGING SYSTEM AND METHOD USING DYNAMIC VISUAL STIMULATION

(71) Applicant: CHONGQING BIO NEWVISION MEDICAL EQUIPMENT LTD., Chongqing (CN)

(72) Inventors: Jun Tao, Chongqing (CN); Gangjun Liu, Chongqing (CN); Wenchao Yu, Chongqing (CN)

(73) Assignee: CHONGQING BIO NEWVISION MEDICAL EQUIPMENT LTD., Chongqing (CN)

( * ) Notice: Subject to any disclaimer, the term of this patent is extended or adjusted under 35 U.S.C. 154(b) by 1143 days.

(21) Appl. No.: 16/965,224

(22) PCT Filed: Jan. 15, 2019

(86) PCT No.: PCT/CN2019/071807
§ 371 (c)(1),
(2) Date: Jul. 27, 2020

(87) PCT Pub. No.: WO2019/200987
PCT Pub. Date: Oct. 24, 2019

(65) Prior Publication Data
US 2020/0345284 A1    Nov. 5, 2020

(30) Foreign Application Priority Data

Apr. 21, 2018  (CN) .......................... 201810363180.8

(51) Int. Cl.
*A61B 5/1455*   (2006.01)
*A61B 3/00*     (2006.01)
(Continued)

(52) U.S. Cl.
CPC ........ *A61B 5/14555* (2013.01); *A61B 3/0025* (2013.01); *A61B 3/12* (2013.01);
(Continued)

(58) Field of Classification Search
CPC ..... A61B 5/14555; A61B 3/12; A61B 5/1103; A61B 5/163; A61B 3/0008; A61B 3/14; A61B 5/161
(Continued)

(56) References Cited

U.S. PATENT DOCUMENTS 5,308,919 A    5/1994  Minnich
5,331,796 A *  7/1994  Varga .................. G02B 6/4491
                                              57/352
(Continued)

FOREIGN PATENT DOCUMENTS

CN    102008287 A    4/2011
CN    102028477 A    4/2011
(Continued)

OTHER PUBLICATIONS

PE2E-SEARCH Machine Translation of CN 107260224 A (Year: 2017).*
(Continued)

*Primary Examiner* — Patrick Fernandes
*Assistant Examiner* — Jonathan E. Cooper
(74) *Attorney, Agent, or Firm* — Steven M. Koehler; Westman, Champlin & Koehler, P.A.

(57) ABSTRACT

The present application discloses a multi-spectral fundus imaging system and method using dynamic visual stimulation, where the imaging system includes: a multi-spectral light source capable of emitting multiple different wavelengths; a mid-pass mirror being a reflecting mirror with a central hole penetrating the reflecting mirror; an imaging focusing lens group; an image acquisition device; and a
(Continued)

controller configured to control the multi-spectral light source and the image acquisition device to work synchronously; a pattern sent by the optical stimulation device is transmitted to the fundus through the image focusing lens group and the central hole of the mid-pass mirror in sequence; an imaging light reflected from the fundus passes through the central hole of the mid-pass mirror and the imaging focusing lens group in sequence; the image acquisition device acquires the image to complete a multi-spectral fundus image acquisition.

7 Claims, 3 Drawing Sheets (51) Int. Cl.
*A61B 3/12* (2006.01)
*A61B 3/14* (2006.01)
*A61B 5/00* (2006.01)

(52) U.S. Cl.
CPC .............. *A61B 3/14* (2013.01); *A61B 5/7267* (2013.01); *A61B 5/7278* (2013.01)

(58) Field of Classification Search
USPC .......................................................... 600/318
See application file for complete search history.

(56) References Cited

U.S. PATENT DOCUMENTS

| | | | | |
|---|---|---|---|---|
| 5,751,396 | A * | 5/1998 | Masuda | A61B 3/145 351/208 |
| 6,478,424 | B1 * | 11/2002 | Grinvald | A61B 3/12 600/476 |
| 7,222,961 | B2 | 5/2007 | Soliz et al. | |
| 9,480,393 | B2 | 11/2016 | Boate et al. | |
| 2003/0157464 | A1 * | 8/2003 | Tanassi | A61B 3/145 434/81 |
| 2004/0085542 | A1 | 5/2004 | Soliz et al. | |
| 2004/0114109 | A1 | 6/2004 | Soliz et al. | |
| 2004/0263784 | A1 * | 12/2004 | Cornsweet | A61B 3/12 351/221 |
| 2005/0280776 | A1 | 12/2005 | Suzuki | |
| 2005/0288565 | A1 * | 12/2005 | Kerr | A61B 5/14555 600/340 |
| 2006/0276698 | A1 | 12/2006 | Halldorsson et al. | |
| 2007/0091265 | A1 * | 4/2007 | Kardon | A61B 3/12 351/206 |
| 2007/0179382 | A1 | 8/2007 | Vilser et al. | |
| 2007/0211211 | A1 | 9/2007 | Soliz et al. | |
| 2009/0153797 | A1 | 6/2009 | Allon et al. | |
| 2009/0153798 | A1 * | 6/2009 | Dick | A61B 5/0261 351/221 |
| 2010/0128221 | A1 * | 5/2010 | Muller | A61B 3/1025 348/78 |
| 2013/0128227 | A1 * | 5/2013 | Cui | A61B 3/10 351/246 |
| 2014/0333898 | A1 | 11/2014 | Boate et al. | |
| 2015/0272438 | A1 * | 10/2015 | Yao | A61B 3/0008 351/246 |
| 2016/0270656 | A1 | 9/2016 | Samec et al. | |
| 2018/0303667 | A1 * | 10/2018 | Peyman | A61B 5/0095 |

FOREIGN PATENT DOCUMENTS

| | | | | |
|---|---|---|---|---|
| CN | 102078182 | A | | 6/2011 |
| CN | 104080394 | A | | 10/2014 |
| CN | 106821302 | A | | 6/2017 |
| CN | 106901687 | A | | 6/2017 |
| CN | 107260224 | A * | 10/2017 | .............. A61B 3/10 |
| CN | 108670192 | A | | 10/2018 |
| JP | 2002204786 | A | | 7/2002 |
| JP | 2007267761 | A | | 10/2007 |
| JP | 2009502220 | A | | 1/2009 |
| JP | 2013501553 | A | | 1/2013 |
| JP | 2014512245 | A | | 5/2014 |
| JP | 2014532514 | A | | 12/2014 |
| JP | 2015123207 | A | | 7/2015 |
| JP | 2016214370 | A | | 12/2016 |
| JP | 2017501854 | A | | 1/2017 |
| JP | 2018051223 | A | | 4/2018 |

OTHER PUBLICATIONS

Written Opinion of the International Searching Authority dated Mar. 28, 2019 for corresponding International Patent Application No. PCT/CN2019/071807, filed Jan. 15, 2019.

International Search Report dated Mar. 14, 2019, for corresponding International Patent Application No. PCT/CN2019/071807, filed Jan. 15, 2019.

* cited by examiner

MULTI-SPECTRAL FUNDUS IMAGING SYSTEM AND METHOD USING DYNAMIC VISUAL STIMULATION

CROSS-REFERENCE TO THE RELATED APPLICATION

The present application claims the priority of CN patent application submitted to the Chinese Patent Office on Apr. 21, 2018, with application No. 201810363180.8, entitled "a multi-spectral fundus imaging system using dynamic visual stimulation", the entire contents of which are incorporated herein by reference.

TECHNICAL FIELD

The present application relates to the fundus imaging technology, and more specifically to a multi-spectral fundus imaging system using dynamic visual stimulation.

BACKGROUND

The fundus refers to the tissue in the posterior part of the eyeball, including the retina, fundus blood vessels, optic nerve head, optic nerve fiber, macular and choroid behind the retina, and so on. The lesions that occur in these areas are collectively called fundus diseases. The retina is a highly complex membrane with a large number of microvascular networks distributed on it. It is the only deeper microvascular network that can be directly observed by non-invasive means in the human body. Observing the blood vessels on the retina of the human eyes can provide doctors with a basis for a diagnosis of many eye diseases and even systemic diseases. For example, hypertension, hyperlipidemia, kidney disease, diabetes, coronary heart disease and other diseases, the changes of physiological state in the early period will be reflected in the fundus.

When the disease causes changes in the state of the fundus, an inspection of the fundus is an effective way to discover and control the condition in time. At present, the clinically effective fundus examination equipment mainly includes ophthalmoscope, slit lamp microscope, fundus camera, scanning laser ophthalmoscope, optical coherence tomography, etc. The fundus camera has become the most widely used fundus inspection equipment at present due to its advantages of good technological development maturity, practicality, easy operation and low production cost. Multi-spectral fundus imaging projects multiple monochromatic light sources into the fundus separately to collect signals reflected by different tissues of the fundus, and different types and/or depths of the tissues may cause optical differences in reflected signals. Compared with the traditional fundus imaging method, multi-spectral fundus imaging has a wide spectral range (500-850 nm), which can perform layer-by-layer and frontal imaging of the retina, realizing non-invasive, direct imaging of the retina and choroid. This method does not require mydriasis, is non-invasive and intuitive, and can improve the accuracy of judgment of the physiological state of the fundus. Traditional multi-spectral fundus imaging mainly focuses on static structural imaging. However, no significant changes in the physiological structure of the fundus have been observed in early patients, so static structural imaging is not suitable for early screening and diagnosis of fundus diseases.

SUMMARY

The present application provides a multi-spectral fundus imaging system and method including a variety of dynamic visual stimulation modes, for example, detecting the response of the fundus to external light stimulation by capturing the physiological state of the fundus before and after different optical stimulation, so as to realize dynamic multi-spectral fundus functional imaging.

One objective of the present application includes providing a multi-spectral fundus functional imaging system combining with dynamic visual stimulation.

As for the present application "multi-spectral fundus functional imaging system combining with dynamic visual stimulation", the imaging system comprises a multispectral light source, a mid-pass mirror, an imaging focusing lens group, an image acquisition device and a controller; the multi spectral light source is a light source capable of emitting a plurality of different wavelengths; the middle pass mirror is a mirror and a central hole penetrating the mirror is arranged on the mirror; the controller controls the multi-spectral light source and the image acquisition device to work synchronously, where the monochromatic excitation light emitted by the multi-spectral light source is reflected into the fundus through the central hole of the mid-pass mirror; the reflected imaging light passes through the central hole of the mid-pass mirror and the imaging focusing lens group in sequence; the image acquisition device acquires a image and a multi-spectral fundus image acquisition is completed; and the multi-spectral light source changes the wavelengths of the excitation lights, and the image acquisition device simultaneously acquires corresponding multi-spectral fundus images of different wavelengths until the images with all the wavelengths are acquired to form a multi-spectral static image;

further includes an optical stimulation device; and the controller controls the optical stimulation device and the image acquisition device to work synchronously, and a pattern sent by the optical stimulation device is transmitted to the fundus through the image focusing lens group and the central hole of the mid-pass mirror in sequence; an imaging light reflected from the fundus passes through the central hole of the mid-pass mirror and the imaging focusing lens group in sequence; the image acquisition device acquires the image to complete multi-spectral fundus image acquisition. The present application extends the multi-spectral fundus static imaging to the dynamic functional imaging by combining dynamic visual stimulation and combines image processing and machine learning to improve the universality and accuracy of methods for diagnosing fundus diseases.

In a preferable embodiment of the present application, further includes providing a first focusing lens at the light path between the multi-spectral light source and the mid-pass mirror, which is beneficial to focus the light source emitted by the multi-spectral light source and prevent the light source from dispersing.

alternatively, providing a first focusing lens at a light path between the multi-spectral light source and the mid-pass mirror, and a light path adjustment device between the first focusing lens and the mid-pass mirror; the light path adjustment device is beneficial to adjust the direction of the light path, making the placement more convenient.

or/and, providing a second focusing lens at the light path between the fundus and the mid-pass mirror, which is beneficial to focus the light source passing through the second focusing lens and prevent the light source from dispersing.

or/and, providing a dichroic lens at the light path between the optical stimulation device and the imaging focusing lens group. The dichroic mirror facilitates the almost complete transmission of light of a certain wavelength and the almost complete reflection of light of other wavelengths. Thereby reflected light or transmitted light is selected according to the actual situation.

In a preferable embodiment of the present application, the multi-spectral light source adopts multiple light-emitting diodes with different wavelengths; According to the different absorption and reflection characteristics of different substances in fundus tissue to each monochromatic light, the image shows the fundus morphological characteristics of different levels and different reflection points, which helps the doctor to more accurately perform the early screening and diagnosis of related ophthalmic diseases. Or/and, the multi-spectral light source comprises a multi-in-one ring-shaped optical fiber bundle which comprises multiple optical fiber branches, a combining end, and a ring-shaped light outlet; ends of the multiple optical fiber branches are the combining end, and the ring-shaped light outlet is disposed at the combining end. The ring-shaped light outlet is disposed at the combining end of the multi-in-one ring-shaped optical fiber bundle, and the emitted light spot is ring-shaped, which is beneficial to reduce the reflection of light on the cornea. The present application simplifies the structure of the fundus camera by using a multi-spectral light source combined with a multi-in-one ring-shaped optical fiber, avoiding the wheel mechanical design of traditional multi-spectral fundus camera, such that the switching between light sources is more rapid and stable, the acquisition time of each set of images is shorter than the reaction time of the human eye, the difficulty of image registration between the set of images is reduced, the reliability of multi-spectral images is improved, and the accuracy of the entire multi-spectral fundus functional imaging is improved.

In a preferable embodiment of the present application, optical fiber filaments of each fiber branch in the multi-in-one ring-shaped optical fiber bundle are evenly distributed throughout an optical fiber filament ring. When LEDs with different wavelengths are lit, the position of the ring-shaped light emitted from the ring-shaped light outlet is basically fixed, thereby achieving fast and displacement-free switching between light sources with different wavelengths under the same set of light paths.

In a preferable embodiment of the present application, a number of the optical fiber branches is greater than or equal to a required number of light-emitting diodes. For LEDs with weak light intensity or LEDs that require filtering to improve monochromaticity, the LED light intensity can be increased by increasing the number of branches of the same type of optical fiber to improve the lighting quality. Each optical fiber branch comprises multiple optical fiber filaments, where the diameter of each optical fiber branch is enough to cover the light-emitting surface of LED with a single lamp bead by the means of fitting coupling mode. The fitting coupling mode can achieve better coupling efficiency.

In a preferable embodiment of the present application, the number of optical fiber filaments included in each optical fiber branch is any value from 100 to 9999.

In the present application, the original white light source is replaced with an optical fiber multi-spectral light source, and the infrared light used for monitoring can also be introduced into the entire system through a fiber branch, such that the light path portion used for infrared monitoring in the traditional fundus camera structure can also be omitted, which greatly simplifies the fundus camera module structure.

In a preferable embodiment of the present application, the image acquisition device is a photographing device or a photography device.

Or/and, the light path adjustment device comprises a focusing lens group and a reflecting mirror.

Or/and, the optical stimulation device is a high-brightness industrial display screen or a micro-projector; by the computer controlling, the different patterns are projected to the fundus through the display screen or micro-projector, which includes multiple patterns of different colors, intensities and different patterns.

Or/and, the controller is a computer.

In a preferable embodiment of the present application, the photographing device is a CCD camera or a CMOS camera. In order to take a complete set of multi-spectral images before the pupils shrink obviously after being illuminated by light, the exposure time of each frame of images is controlled on the order of tens of milliseconds, which greatly increase the sensitivity required for the camera. In the present application, a scientific-grade CMOS camera is adopted to be able to meet the sensitivity requirement of short-term exposure. In addition, under the condition of extremely short exposure, the human eye is approximately kept at rest, and there is no obvious displacement deviation between the frames of the multi spectral images, which greatly reduces the image registration requirements.

In a preferable embodiment of the present application, the wavelengths of the light emitted by the multi-spectral light source comprise one or more selections from a group of 500 nm, 530 nm, 570 nm, 600 nm, 630 nm, and 850 nm. The different wavelengths correspond to different fundus levels: blue-green light (500 nm) shows the superficial retinal structure, which is used to observe the anterior retinal membrane, retinal nerve layer, retinal folds, cysts and macular holes, etc.; green light (530 nm), yellow light (570 nm), and amber light (600 nm) show the middle-layer retinal structure, which are used to observe bleeding, exudation and drusen, neovascularization and other diseases, such as diabetic retinopathy; red light (630 nm) and near infrared light (850 nm) show the deep layer retinal structure, which is used to observe the lesions associated with retinal pigment disorders, RPE layer degeneration, macular degeneration, choroidal melanoma and so on.

Another objective of the present application includes providing an imaging method of the multi-spectral fundus imaging system using dynamic visual stimulation, and the imaging method includes the following steps:

1) acquiring a multi-spectral image before applying optical stimulation:

a) monitoring mode:

the camera first works in an infrared light monitoring mode after starting, adjusting the relative position of the system and the fundus of the subject, and adjusting the focusing to find an interesting area of the subject's fundus;

b) external trigger mode:

after finding the interest area of the subject's fundus, the camera works in an external or internal trigger mode, and the computer controls the multi-spectral light source to synchronize with the camera, where the monochromatic excitation light emitted by the multi-spectral light source passes through a multi-in-one ring-shaped optical fiber bundle and outputs from a ring-shaped light output to form a ring-shaped light; the ring-shaped light is focused and changed by a first focusing lens and light path adjustment device; and reflected around the central hole of a mid-pass mirror;

entering into the fundus after focused by a second focusing lens; the reflected imaging light from the fundus is focused by the focusing lens to the central hole of the mid-pass mirror again while passing through the central hole; then passing through the imaging focusing lens group and entering the camera. The computer controls the multi-spectral light source and the camera to perform static imaging to complete one multi-spectral fundus image acquisition;

c) the multi-spectral light source changes the wavelength of the excitation light and the computer controls the multi-spectral light source to synchronize with the camera, the camera simultaneously takes corresponding multi-spectral fundus images of the corresponding wavelength, and steps a) and b) are repeated until all wavelengths are taken;

d) transmitting to the computer to form a set of multi-spectral images;

2) applying optical stimulation:

a) adjusting a dichroic mirror to enter the light path; and the computer controls the optical stimulation device to send a pattern, which is reflected by the dichroic mirror, passes through the imaging focusing lens group, the central hole of the mid-pass mirror, and the second focusing lens in sequence, and then transmits to the fundus; the contrast between light and dark in the pattern corresponds to the strength of the optical stimulations to the fundus tissue when the dynamic stimulation of the fundus tissue is regulated;

b) when the optical stimulation ends, turning off the optical stimulation device and moving the dichroic mirror out of the light path;

3) acquiring multiple sets of multi-spectral images in time series after applying optical stimulation:

according to the method in step 1), performing multi-spectral image acquisition at different time points by the camera on the fundus after optical stimulation, and transmitting it to the computer;

calculating a blood oxygen saturation value:

4) constituting functional imaging by multiple static imaging at different time points before and after applying of optical stimulation, calculating the blood oxygen saturation value by a computer according to the multiple multi-spectral images at different time points before and after the applying of optical stimulation, and monitoring a dynamic blood oxygen saturation value to evaluate the dynamic response and recovery of the fundus circulation and nervous system to optical stimulation.

In a preferable embodiment of the present application, in step 4), calculating the blood oxygen saturation value and monitoring the dynamic blood oxygen saturation value comprises the steps of:

performing a preprocessing of the fundus images of multi-spectral images at different wavelengths at the same time by the computer, where the preprocessing includes image unevenness correction, light intensity correction and image denoising;

performing a blood vessels segmentation of the fundus images after preprocessed by a network model obtained by pre-training and being verified to obtain the segmented images; wherein the network model is a model for the blood vessels segmentation calculation based on deep learning algorithms;

performing a binarization processing and centerline extraction on the segmented image, traversing each point R (i, j) of the centerline, and searching for points at 8-connected neighborhoods corresponding to each point, to complete the traversing and searching for the entire blood vessel; wherein (i, j) represents horizontal and vertical positions in the image, and R represents the gray value of the point;

calculating an optical density value of each segment of blood vessels under the light of specified wavelength based on the results of traversing and searching for the blood vessels;

calculating the blood oxygen saturation according to the optical density value of each segment of blood vessels under the light of specified wavelength light; and outlining a region of interest of the fundus image by controlling an image acquisition frequency, and performing the monitoring of the dynamic blood oxygen saturation value based on the region of interest.

In a preferable embodiment of the present application, the method further includes:

obtaining training samples and verification samples; wherein the training samples and the verification samples each comprise multiple sets of samples, and each set of samples comprises a fundus image and a corresponding manual segmentation image;

using the fundus images of the training samples as an input of a deep full convolution network, and using the corresponding manual segmentation images as an output of the deep full convolution network, to achieve hyperparameter optimization and to train the deep full convolution network;

using the fundus images of the verification samples as an input of a deep full convolution network, and using the corresponding manual segmentation images as an output of the deep full convolution network, to verify the deep full convolution network;

determining the deep full convolution network with the highest segmentation accuracy as a network model configured for segmenting blood vessels of different wavebands of fundus images in the multi-spectral images.

In a preferable embodiment of the present application, the step of obtaining training samples and verification samples comprises:

performing a manual segmentation of multiple fundus images at the same wavelength by an ophthalmologist to obtain manual segmentation image of each fundus image;

making a set of samples according to the fundus images and its corresponding manual segmentation images based on each manual segmentation image of the obtained fundus image, and the number of the samples is larger than 100; using a part of the samples as the training samples, using another part of the samples as the verification samples, and the number of verification samples is greater than 20.

In a preferable embodiment of the present application, the network model is a full convolution network structure comprising at least 10 convolutional layers.

In a preferable embodiment of the present application, the steps of calculating the optical density value of each segment of blood vessels under the light of specified wavelength light comprise:

calculating the optical density value of each segment of blood vessels by the following formula:

$$OD_\lambda = lg\frac{I_0}{I} = \varepsilon_{Hbo2}C_{Hbo2}d + \varepsilon_{Hb}C_{Hb}d$$

among then, I represents an intensity of the incident light after passing through the solution, $I_0$ represents intensity of original incident light, ε represents absorption coefficient of the solution, C represents the concentration of the solution, d represents the distance of light passing through the solution, $C_{Hbo2}$ represents absorption coefficient of oxygen and hemoglobin solution, $\varepsilon_{Hb}$ represents absorption coefficient of hemoglobin solution, $C_{Hbo2}$ represents solution concentration of oxygen and hemoglobin and $C_{Hb}$ represents solution concentration of hemoglobin.

In a preferable embodiment of the present application, the steps of calculating the blood oxygen saturation according to the optical density value of each segment of blood vessels under the light of specified wavelength comprise:

calculating the blood oxygen saturation by the following formula:

$$SO_2 = a \cdot ODR + b$$

among then, $ODR = OD_{unequal\ absorption}/OD_{equal\ absorption}$ represents a ratio of the optical density with an unequal absorption coefficient to the optical density with equal absorption coefficient, and a and b are constant.

DETAILED DESCRIPTION

The embodiments of the present application are described in detail below. Examples of the embodiments are shown in the drawings, in which the same or similar reference numerals indicate the same or similar components or components having the same or similar functions. The embodiments described below with reference to the drawings are exemplary, and are only used to explain the present application, and cannot be construed as a limitation of the present application.

In the description of this application, it should be understood that the orientation or positional relationship indicated by the terms "longitudinal", "horizontal", "upper", "lower", "front", "back", "left", "right", "vertical", "top", "bottom", "inner", "outer", etc. are based on the orientation or positional relationship shown in the drawings, and is only for the convenience of describing the application and simplifying the description, not the indication or suggestion that the device or components must have a specific orientation, be constructed and operated in a specific orientation, and therefore cannot be construed as a limitation of the present application.

In the description of this application, unless otherwise specified and limited, it should be noted that the terms "installation", "connection", and "connecting" should be understood in a broad sense, for example, it may be a mechanical connection or an electrical connection, or an internal communication of two components, or may be directly connected or indirectly connected through an intermediate medium. For those skilled in the art, the specific meaning of the above terms can be understood according to specific circumstances.

Considering that the traditional multi-spectral fundus imaging mainly focuses on static structure imaging, and the fundus of early patients usually has not been able to be observed significant physiological structural changes, the static structural imaging is difficult to apply to the early screening and diagnosis of fundus diseases. In order to improve this problem, the present application creatively proposes to realize dynamic fundus functional imaging by using a variety of optical stimulation methods and by monitoring the changes of optical properties caused by other mechanisms such as blood oxygen saturation. For example, by capturing the physiological state of the fundus before and after different optical stimulation, and detecting the response of the fundus to external light stimulation, the dynamic multi-spectral fundus functional imaging is realized.

In addition to the circulatory system, since the activity of the optic nerve system of the fundus depends on the support of cellular metabolic functions, when the optic nerve is activated, its response will also be partially reflected in the blood oxygen saturation index, such that the blood oxygen saturation becomes a functional index of studying the fundus nerve and circulatory system in the early stage of the disease, providing a revolutionary new technology for the early diagnosis of fundus disease.

In the following, the present application will be further described through specific embodiments with reference to the drawings.

Figure 1:
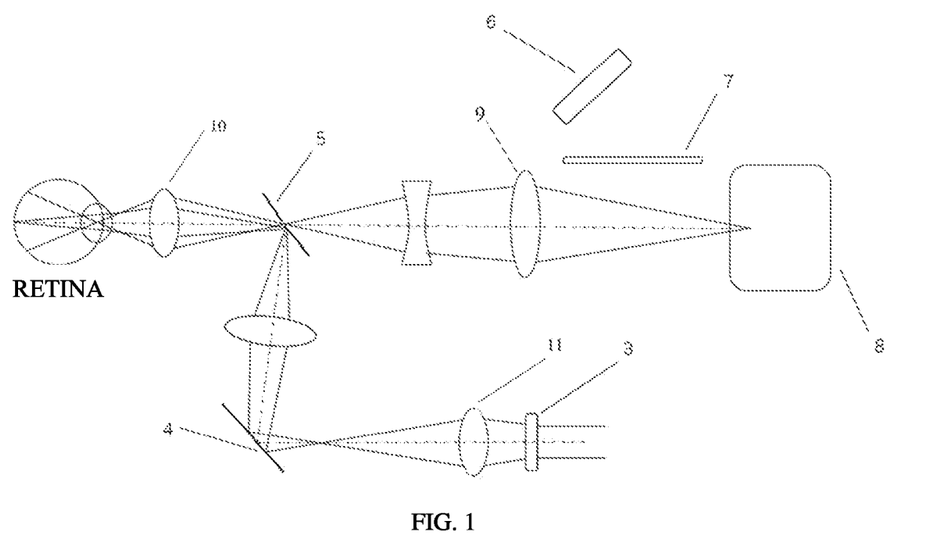
FIG. 1 is a schematic view of a light path of an embodiment according to a multi-spectral fundus imaging system using dynamic visual stimulation according to the present application.

As shown in FIG. 1, the multi-spectral fundus imaging system using dynamic visual stimulation of this embodiment includes a multi-spectral light source 3, a first focusing lens 11, a light path adjustment device 4, a mid-pass mirror 5, a second focusing lens 10, and an imaging focusing lens group 9, an image acquisition device 8, an optical stimulation device 6, a dichroic mirror 7 and a controller.

In some embodiments, the first focusing lens 11 is provided on the light path between the multi-spectral light source 3 and the mid-pass mirror 5; among then, one of the functions of setting the first focusing lens includes: be beneficial to focus the light source emitted by the multi-spectral light source and prevent the light source from dispersing. And/or, the light path adjustment device 4 is provided on the light path between the first focusing lens 11 and the mid-pass mirror 5; one of the functions of setting the light path adjustment device 4 includes: be beneficial to adjust the direction of the light path, and make the placement of the system more convenient.

And/or, the second focusing lens 10 is provided on the light path between the fundus and the mid-pass mirror 5; one of the functions of setting the second focusing lens includes: be beneficial to focus the light source emitted by the second focusing lens and prevent the light source from dispersing.

And/or, the dichroic mirror 7 is provided on the light path between the optical stimulation device 6 and the imaging focusing lens group 9. The dichroic mirror 7 is also called a dichroscope, and the dichroic mirror facilitates the almost complete transmission of light of certain wavelengths, and the reflection of light of other wavelengths almost completely. Thereby the reflected light or transmitted light should be selected according to the actual situation.

In the embodiment, the multi-spectral light source is a light source that can emit multiple different wavelengths, or a light source that emits the same wavelength at the same time, or a light source that emits different wavelengths at the same time; the mid-pass mirror is a reflecting mirror with a central hole penetrating the reflecting mirror; the structure of mid-pass mirror can also be expressed as the mid-pass mirror includes a reflecting mirror and a central hole disposed on the reflecting mirror, and the central hole penetrates the reflecting mirror; the light path adjustment device includes the focusing lens group and the reflecting mirror, and the focusing lens group includes one or more focusing lenses. The light path adjustment device can set the light path according to the actual situation; in some embodiments, the optical stimulation device is a high-brightness industrial display screen or a micro-projector; the controller is a computer or a device with processing function. With the control of the controller, the optical stimulation device can project the patterns of different modes (pattern color, light intensity, pattern style, etc.) to the fundus.

In practical applications, the controller controls the multi-spectral light source 3 and the image acquisition device 8 to work synchronously, a monochromatic excitation light emitted by the multi-spectral light source 3 is reflected into the fundus through the central hole of the mid-pass mirror 5, and a reflected imaging light passes through the central hole of the mid-pass mirror 5 and the imaging focusing lens group 9 in sequence; and the image acquisition device 8 acquires an image and completes a multi-spectral fundus image acquisition.

The multi-spectral light source 3 changes the wavelength of the monochromatic excitation light, and the image acquisition device 8 simultaneously acquires corresponding multi-spectral fundus images of different wavelengths until all the wavelengths are acquired to form a multi-spectral static image. In practical applications, the wavelength of the light emitted by the multi-spectral light source (3) comprises one or more selections from a group of 500 nm, 530 nm, 570 nm, 600 nm, 630 nm, and 850 nm. The different wavelengths correspond to different fundus levels: blue-green light (500 nm) shows the superficial retinal structure, which is used to observe the anterior retinal membrane, retinal nerve layer, retinal folds, cysts and macular holes, etc.; green light (530 nm), yellow light (570 nm), and amber light (600 nm) show the middle-layer retinal structure, which is used to observe bleeding, exudation and drusen, neovascularization and other diseases, such as diabetic retinopathy; red light (630 nm) and near infrared light (850 nm) show the deep layer retinal structure, which is used to observe the lesions associated with retinal pigment disorders, RPE layer degeneration, macular degeneration, choroidal melanoma and so on.

Figure 2:
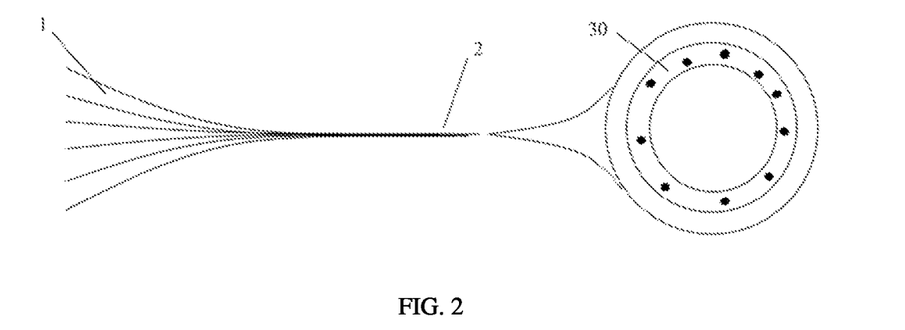
FIG. 2 is a schematic view of a multi-in-one ring-shaped optical fiber according to a multi-spectral fundus imaging system using dynamic visual stimulation according to the present application.

In one embodiment, the multi-spectral light source 3 adopts multiple light-emitting diodes with different wavelengths; in an embodiment, the multi-spectral light source comprises a multi-in-one ring-shaped optical fiber bundle, and the multi-in-one ring-shaped optical fiber bundle comprises multiple optical fiber branches, a combining end, and a ring-shaped light outlet; the ends of multiple optical fiber branches are the combining end, and the ring-shaped light outlet is disposed at the combining end. As shown in FIG. 2, the multi-in-one ring-shaped optical fiber bundle includes multiple optical fiber branches 1, a combining end 2 and a ring-shaped light outlet 30; the ends of multiple optical fiber branches 1 are the combining end 2, and the ring-shaped light outlet 30 is disposed at the combining end 2. The ring-shaped light outlet is disposed at the combining end of the multi-in-one ring-shaped optical fiber bundle, and the emitted light spot is ring-shaped, which is beneficial to reduce the reflection of light on the cornea.

The present application simplifies the structure of the multi-spectral fundus imaging system (also called multi-spectral fundus camera) by using a multi-spectral light source combined with a multi-in-one ring-shaped optical fiber, avoiding the wheel mechanical design of traditional multi-spectral fundus camera, such that the switching between light sources is more rapid and stable, the acquisition time of each set of images is shorter than the reaction time of the human eye, the difficulty of image registration between the set of images is reduced, the reliability the multi-spectral images is improved, and the accuracy of the entire multi-spectral fundus functional imaging is improved.

In a specific embodiment of the present application, optical fiber filaments of each fiber branch in the multi-in-one ring-shaped optical fiber bundle are evenly distributed throughout an optical fiber filament ring. When LEDs with different wavelengths are lit, the position of the ring-shaped light emitted from the ring-shaped light outlet is basically fixed, thereby achieving fast and displacement-free switching between light sources with different wavelengths under the same set of light paths.

In a specific embodiment of the present application, the number of optical fiber branches is greater than or equal to the required number of light-emitting diodes. For LEDs with weak light intensity or LEDs that require filtering to improve monochromaticity, the LED light intensity can be increased by increasing the number of branches of the same type of optical fiber to improve the lighting quality. The number of optical fiber filaments included in each optical fiber branch is any value from 100 to 9999, each optical fiber branch comprises multiple optical fiber filaments, and the diameter of each optical fiber branch covers the light-emitting surface of LED with a single lamp bead, adopting a fitting coupling mode. The fitting coupling mode can achieve better coupling efficiency.

The controller controls the multi-spectral light source 3 and the image acquisition device 8 to work synchronously, and a pattern sent by the optical stimulation device 6 is transmitted to the fundus through the image focusing lens group 9 and the central aperture of the mid-pass mirror 5 in sequence; an imaging light reflected from the fundus passes through the central hole of the mid-pass mirror 5 and the imaging focusing lens group 9 in sequence; the image acquisition device acquires the image to complete a multi-spectral fundus image acquisition. In practical applications, the image acquisition device 8 is a photographing device or a photography device. The photographing device can adopt a charge coupled device (CCD) camera or a Complementary Metal Oxide Semiconductor (CMOS) camera.

In order to take a complete set of multi-spectral images before the obvious pupils shrink after being illuminated by light, the exposure time of each image is controlled on the order of tens of milliseconds, and the sensitivity required for the camera is greatly increased. In the present application, a scientific-grade CMOS camera is adopted to be able to meet the sensitivity requirement of short-term exposure. In addition, under the condition of extremely short exposure, the human eye remains approximately at rest, and there is no significant displacement deviation between the results of the captured multi-spectral images, which greatly reduces the image registration requirements.

It should be noted that FIG. 1 only shows one embodiment of the multi-spectral fundus imaging system. In practical applications, other embodiments may also be used, including more or less components than the system in FIG. 1, which is not limited herein.

To facilitate understanding, the static imaging and functional imaging are taken as examples to illustrate the working principle of multispectral fundus imaging system as follows: (1) Under static imaging: the monochromatic excitation light (also called monochromatic light) emitted by the multi-spectral light source passes through the multi-in-one ring-shaped optical fiber bundle and output from the ring-shaped light outlet to form a ring-shaped light; the ring-shaped light is focused by the first focusing lens 11, whose light path is adjusted by the light path adjustment device 4 to emit the mid-pass mirror, and then reflected around the central hole of the mid-pass mirror 5; after being focused by the second focusing lens 10, it enters into the fundus; the imaging light reflected from the fundus is then focused by the second focusing lens 10 to the central hole of the mid-pass mirror 5 and passes through the central hole; the imaging light passing through the central hole passes through the imaging focusing lens group 9 and enters the image acquisition device.

(2) Under functional imaging: the dichroic mirror 7 is adjusted to enter the light path; the controller controls the optical stimulation device 6 to send a pattern, and the pattern reflected or transmitted by the dichroic mirror 7 passes through the imaging focusing lens group 9, the central hole of the mid-pass mirror 5, and the second focusing lens 10 in sequence and transmits to the fundus; the contrast between light and dark in the pattern corresponds to the strength of the optical stimulations to the fundus tissue, and regulating the patterns emitted by the optical stimulation device 6 can dynamically stimulate the fundus tissue; the image acquisition device 8 acquires multi-spectral images of the fundus after optical stimulation multiple times at different time points; and then the acquired multi-spectral images are transmitted to the controller, such that the controller performs analysis based on the acquired multi-spectral images.

With the multi-spectral fundus imaging system described above, the fundus can be detected based on the detection index of the fundus physiological state. Taking the detection index as blood oxygen saturation as an example, a basic premise of noninvasive measurement of blood oxygen saturation in the fundus is that oxyhemoglobin and deoxyhemoglobin have different optical absorption coefficients. Therefore, the multi-spectral fundus imaging system must use at least two different wavelengths of light to detect the fundus. For example, two different wavelengths are selected such that oxyhemoglobin and deoxyhemoglobin have the same absorption coefficient in one wavelength of light, and oxyhemoglobin and deoxyhemoglobin have different absorption coefficients in another wavelength of light. In an embodiment, two wavelengths of light of 570 nm and 600 nm can be selected. For the wavelength of light of 570 nm, since the absorption coefficients of oxyhemoglobin and deoxyhemoglobin at this wavelength are equal, therefore, the wavelength of light of 570 nm is not sensitive to blood oxygen saturation; for the wavelength of light of 600 nm, since the absorption coefficients of oxyhemoglobin and deoxyhemoglobin at this wavelength are quite different, the wavelength of light of 600 nm is sensitive to blood oxygen saturation. The retinal fundus images under these two wavelengths of light can be selected to calculate the retinal blood oxygen saturation.

In order to have a further understanding of the multi-spectral fundus imaging system, the application examples of the two multi-spectral fundus imaging systems are given below:

Example 1

This example refers to static and dynamic multi-spectral fundus functional imaging of diabetic patients to evaluate the effect of diabetes progression on fundus circulation and neurophysiological status.

About 70% of diabetic patients will have systemic small blood vessel and microvascular disease, which affects the supply of systemic tissues, in turn leads to a series of serious complications. Diabetes can also cause a series of eye diseases, including cataracts, glaucoma, eye movement disorders, etc. Among them, the most serious eye disease is diabetic retinopathy, which is a disease that seriously affects vision and has become one of the major blinding diseases. According to relevant statistics, the longer the duration of diabetes is, the greater the rate of retinopathy. Early patients do not have any feelings, but it is the best time to prevent the disease, finding abnormalities in the early lesion can greatly improve the diagnosis rate of the disease and avoid finding it too late.

The blood glucose index and the blood oxygen saturation index are the two major monitoring points of this example. This example selects diabetic patients in different disease stages and healthy people of the same ages as comparison, measures the blood glucose indexes of all diabetic patients, and groups them according to different disease stages of diabetic patients. For patients and healthy people of the same ages in the same group, the multi-spectral fundus imaging results at rest state are measured, and the oxygen saturation of the fundus at rest state is calculated by the image processing module in the controller of the multi-spectral fundus imaging system; after applying the same optical stimulations, select several time points again to obtain the multi-spectral fundus imaging result map corresponding to each time point, and calculate the dynamic change trend of the blood oxygen saturation of the fundus after receiving the optical stimulations.

For the same patient, the light and dark patterns used in the optical stimulation form optical stimulations of different light intensities of the fundus retina. The trend of blood oxygen saturation can be analyzed between different areas of the fundus to find the influence of different intensity of light stimulation on the dynamic changes of blood oxygen saturation; for patients and healthy people in the same group, the difference of the entire fundus can be compared to find changes in the response of the fundus retinal tissue to light stimulation caused by the lesion.

The image processing module in the controller has two functions: the first is to calculate the retinal blood oxygen saturation of the fundus according to the light of two different wavelengths (such as 570 nm and 600 nm) of the multispectral fundus camera system to obtain the blood oxygen saturation value at a certain moment; the second is to choose the imaging area of interest, local blood vessel area or the entire blood vessel area for dynamic light stimulation blood oxygen saturation monitoring, which is used for the detection of different visual diseases and the study of blood oxygen metabolism of the vascular system and nervous system.

According to Lambert's law, the intensity of light after passing through the solution has the following relationship with the original intensity:

$$I = I_0 \cdot 10^{\varepsilon \cdot c \cdot d} \tag{1.1}$$

Among then, I represents the intensity of the incident light after passing through the solution, $I_0$ represents the intensity of the original incident light, $\varepsilon$ represents the absorption coefficient of the solution, c represents the concentration of the solution, and d represents the distance of the light passing through the solution.

The optical density function under the light of wavelength λ is defined as follows:

$$OD_\lambda = lg\frac{I_0}{I} = \varepsilon_{Hbo2}C_{Hbo2}d + \varepsilon_{Hb}C_{Hb}d \qquad (1.2)$$

For the blood, the optical density function under the light of wavelength λ is defined as follows:

$$OD_\lambda = lg\frac{I_0}{I} = \varepsilon_{Hbo2}C_{Hbo2}d + \varepsilon_{Hb}C_{Hb}d \qquad (1.3)$$

Among then, $\varepsilon_{Hbo2}$ represents the absorption coefficient of the oxygen and hemoglobin solution, $\varepsilon_{Hb}$ represents the absorption coefficient of the hemoglobin solution, $C_{Hbo2}$ represents the concentration of the oxygen and hemoglobin solution, and $C_{Hb}$ represents the concentration of the hemoglobin solution;

Thereby, a ratio of the optical density with unequal absorption coefficient to the optical density with equal absorption coefficient is:

$$ODR = OD_{unequal\ absorption}/OD_{equal\ absorption} \qquad (1.4)$$

The optical density function is a function related to the absorption coefficient, the concentration of the solution, and the distance traveled by light passing through the solution sample. For optical density functions with unequal absorption coefficients, the value depends on the distance, total hemoglobin concentration and blood oxygen saturation; while the value of the optical density function with equal absorption coefficients is only related to the distance and the total hemoglobin concentration, therefore, their ratio ODR is linearly related to the blood oxygen saturation $SO_2$, that is:

$$SO_2 = a \cdot ODR + b \qquad (1.5)$$

Among then, a and b are constant, and by calibrating them, the oxygen saturation value of each segment can be calculated. For blood oxygen saturation detection of fundus imaging, it is difficult to directly measure the intensity of transmitted light, so the intensity of reflected light is used instead of the intensity of transmitted light. $I_0$ and I of the above formula are estimated based on the reflected light intensity of the fundus. $I_0$ represents the light intensity reflected by the background near the retinal blood vessels, which does not pass through the blood vessels, so it is not affected by the blood vessels; I represents the light intensity reflected by the blood vessel and attenuated by the blood vessel. After the fundus image is obtained, the incident light intensity and the transmitted light intensity can be expressed by the pixel value of the area near the blood vessel and the pixel value of the blood vessel, respectively. In this way, by selecting the value of background pixels near the blood vessel, the size of $I_0$ and I are affected by the same factors, only the reflection in the blood vessel is different from that in the background area. The emitted light intensity I represents the minimum gray value in the pixel segment inside the blood vessel, and the incident light intensity $I_0$ represents the average gray value in the pixel segment outside the blood vessel.

Figure 3:
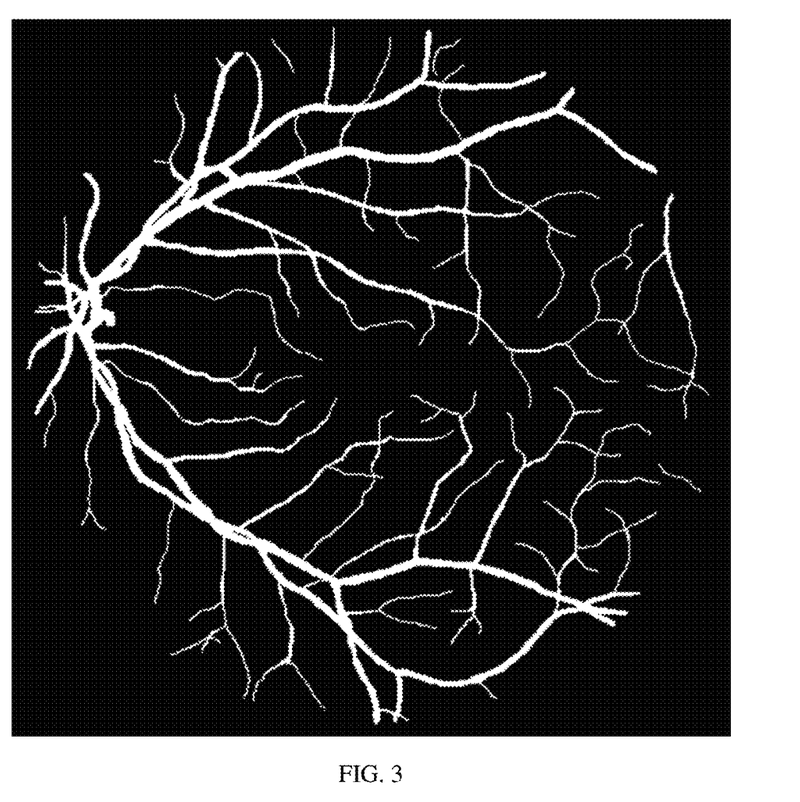
FIG. 3 is a schematic view of a result of performing vascular segmentation on a fundus retinal image by a multi-spectral fundus imaging method using dynamic visual stimulation according to the present application.
Figure 4:
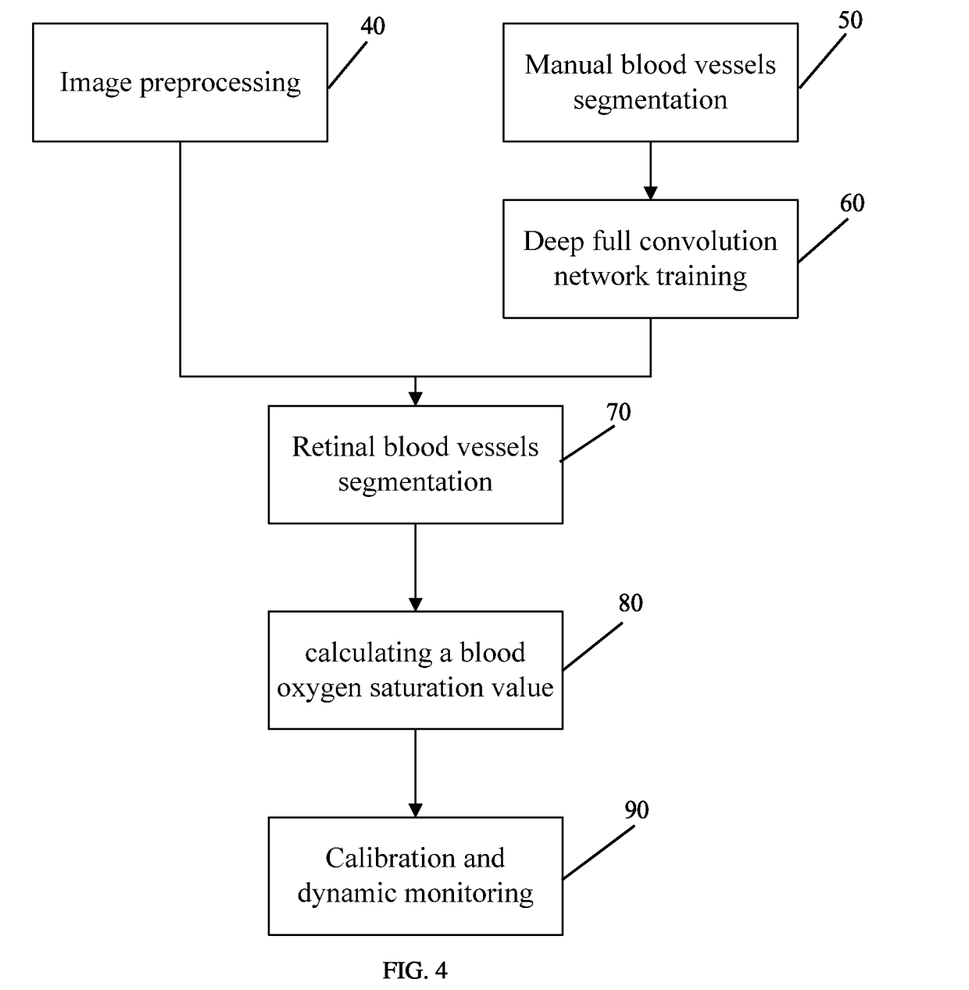
FIG. 4 is a schematic view of a blood oxygen saturation calculation and monitoring process of a multi-spectral fundus function imaging method combined with dynamic visual stimulation according to the present application.

The image processing module performs manual segmentation and labeling on 100 fundus images with a wavelength of 570 nm by experts, obtaining a schematic diagram of the result of the blood vessel segmentation of the fundus retinal image shown in FIG. 3. Using more than 20 images with a wavelength of 570 nm and their segmentation results as verification, and the deep full convolution network model with the highest segmentation accuracy is selected to segment blood vessels of the fundus images of different wavebands in the multi-spectral image. The experiment proves that the deep learning segmentation method based on supervised learning has better segmentation accuracy than traditional morphological processing, template matching, multi-scale filtering and unsupervised segmentation algorithms, which provides the necessary conditions for accurate calculation of blood oxygen saturation. In some embodiments, the wavelength of 570 nm corresponds to an equal absorption coefficient, and the wavelength of 600 nm corresponds to an unequal absorption coefficient. As shown in FIG. 4, when the images with the wavelength of 570 nm and 600 nm acquired at each moment are sent to the image processing module, the image processing module preprocesses the images, including image unevenness correction, light intensity correction, and image denoising and so on. The model trained by the deep full convolutional network is used to segment the blood vessel of the image with the wavelength of 570 nm to obtain accurate blood vessel segmentation results. Then perform binarization processing and center line extraction on the segmented image, traverse each point R (i, j) of the center line, and search for points of 8-connected neighborhoods corresponding to each point, to complete the traversing and searching for the entire blood vessel; the emitted light intensity I represents the minimum gray value in the pixel segment inside the blood vessel, and the incident light intensity $I_0$ represents the average gray value in the pixel segment outside the blood vessel, calculating the optical density value of each segment of the blood vessel through the formula (1.3), and calculating the blood oxygen saturation through the formulas (1.4) and (1.5). By controlling the frequency of image acquisition and outlining the region of interest in the image, the dynamic blood oxygen saturation value monitoring can be performed.

Since the detection method of the present application is non-destructive and non-invasive, different modes of optical stimulation can be further used. Different modes of optical stimulation can be expressed as one or more selections from different optical light and dark patterns, different stimulation times, different stimulation brightness, and different light wavelengths, etc., fully exploring the fundus circulation and the dynamic response process of the nervous system to light stimulation, looking for characteristic changes that can help early diagnosis of the disease.

Example 2

This example refers to static and dynamic multi-spectral fundus functional imaging of experimental animals in the state of blood vessel damage to evaluate the effect of fundus blood vessel damage on the peripheral circulation and neurophysiological state.

Since the laser is widely used in the treatment of fundus diseases, the leakage points can be closed and the retinal edema can be reduced through the laser photocoagulation of the fundus; photocoagulation can also destroy the capillary occlusion area to reduce the formation of neovascularization factors and promote the withdrawal of existing neovascularization to prevent neovascularization and preserves useful visual function. In addition, in a few cases, when the laser is not used properly, it will cause irreversible permanent damage to the fundus. In this example, dynamic functional imaging can be used to evaluate the effect of fundus vascular injury on the peripheral circulation and neurophysiological state. The blood oxygen saturation is still used as the main detection index, combined with optical coherence tomography, fluorescence contrast and other means to evaluate the state of vascular injury, explore the relationship between the two, and exploit new methods for the treatment and subsequent evaluation of fundus diseases.

In this example, rabbits with different degrees of fundus vascular injury (hereinafter referred to as injured rabbits) were used as comparisons with healthy rabbits of the same weight to evaluate the damage status of all injured rabbits with fundus vascular injury and group them according to different disease states. Measuring the multi-spectral fundus imaging results of injured rabbits and healthy rabbits of the same weight in the same group at rest, and calculating the oxygen saturation of the fundus at rest by the image processing module; after applying the same optical stimulation, selecting several time points again, to obtain the corresponding multi-spectral fundus imaging result map at each time point, and to calculate the dynamic change trend of the fundus blood oxygen saturation after receiving optical stimulation.

For the same rabbit, the light and dark patterns used in the optical stimulation form optical stimulations of different light intensities to the fundus retina. The trend of blood oxygen saturation can be analyzed between different areas of the fundus to find the influence law of different intensity of light stimulation on the dynamic changes of blood oxygen saturation; for the injured rabbits and healthy rabbits in the same group, the changes of the fundus retinal tissue response to light stimulation caused by the injury can be found by comparing the entire fundus.

The present application further provides an imaging method of multi-spectral fundus imaging system using dynamic visual stimulation, where the imaging method mainly includes the following steps 1) to 4):

1) acquiring a multi-spectral image before applying optical stimulation:

a) monitoring mode:

after starting the monitoring mode, the image acquisition device (which can be implemented with a camera, taking the camera as an example in the following) of the multi-spectral fundus imaging system first works in an infrared light monitoring mode, adjusting the relative position of the system and the fundus of a subject, and adjusting the focusing to find an interesting area of the subject's fundus.

b) external trigger mode:

After finding the interest area of the subject's fundus, the camera (that is imaging acquisition device) works in an external or internal trigger mode, and the controller of the multi-spectral fundus imaging system (which can be implemented with a computer, taking the computer as an example in the following) controls the multi-spectral light source to synchronize with the camera. The monochromatic excitation light emitted by the multi-spectral light source passes through a multi-in-one ring-shaped optical fiber bundle and is output from a ring-shaped light outlet to form a ring-shaped light; the ring-shaped light is focused and changed by a first focusing lens and light path adjustment device; and reflected around a central hole of an amid-pass mirror; entering the fundus after focused by a second focusing lens; the reflected imaging light from the fundus is focused by the focusing lens to the central hole of the mid-pass mirror and passes through the central hole; then passing through the imaging focusing lens group and entering the camera; the computer (that is the controller) controls the multi-spectral light source and the camera to perform static imaging to complete a multi-spectral fundus image acquisition;

c) the multi-spectral light source changes the wavelength of the excitation light and the computer controls the multi-spectral light source to synchronize with the camera, where the camera simultaneously takes corresponding multi-spectral fundus images of the corresponding wavelength, and steps a) and b) are repeated until all wavelengths are taken;

d) transmitting to the computer to form a set of multi-spectral images;

2) applying optical stimulation:

a) adjusting a dichroic mirror to enter the light path; and the computer controls the optical stimulation device to send a pattern which is reflected by the dichroic mirror, and then passes through the imaging focusing lens group, the central hole of the mid-pass mirror, and the second focusing lens in sequence, and transmits to the fundus; the contrast between light and dark in the pattern corresponds to the strength of the optical stimulations to the fundus tissue, and regulating the patterns emitted by the optical stimulation device can dynamically stimulate the fundus tissue;

b) when the optical stimulation ends, turning off the optical stimulation device and moving the dichroic mirror out of the light path.

3) acquiring multiple sets of multi-spectral images in time series after applying optical stimulation:

according to the method in step 1), performing multi-spectral image acquisition at different time points on the fundus by the camera after optical stimulation, and transmitting it to the computer;

calculating a blood oxygen saturation value:

4) constituting functional imaging by multiple imaging at different time points before and after applying of optical stimulation, and calculating the blood oxygen saturation value by a computer according to the multiple multi-spectral images at different time points before and after the applying of optical stimulation, and monitoring a dynamic blood oxygen saturation value to evaluate the dynamic response and recovery of the fundus circulation and nervous system to optical stimulation. In the embodiment, calculating the blood oxygen saturation value and monitoring the dynamic blood oxygen saturation value includes the steps of:

Step 40. performing a preprocessing of the fundus images in multi-spectral images at different wavelengths by the computer at the same time, the preprocessing comprising image unevenness correction, light intensity correction and image denoising; in a specific embodiment, the image is appropriately stretched and transformed through a preset computer program to perform non-linear correction compensation for non-uniform deformations that may occur at the edge of the image, to ensure that the fundus imaging result is uniform and true. If the light intensity is not uniform enough, the computer software can also automatically detect the difference based on the central brightness of different areas, so as to find local areas that are too bright or too dark. Then, by the method of brightness compensation, the gray value of the display pixels in the area is adjusted, and the light intensity is uniformly corrected in the display result. If there is noise, the interference of image noise can be removed by filtering algorithms in the software such as median filtering or spatial low-pass filtering.

Step 50. performing a manual segmentation by an ophthalmologist onto multiple fundus images at the same wavelength, among then, the specific process of the manual segmentation by the ophthalmologist including in the professional ophthalmology software, the ophthalmologists use the mouse to draw a binary map of the outline of blood vessels based on the observed arteriovenous and capillary blood vessels at various levels of the retina; making a set of samples according to the fundus images and its corresponding manual segmentation images based on each manual segmentation image of the obtained fundus image, the number of the samples is larger than 100; using a part of the samples as the training samples, using another part of the samples as the verification samples, the number of verification samples is greater than 20.

Step 60. establishing a deep fully convolutional network, and using the established deep full convolutional network as the model of a deep learning algorithm for segmentation calculation, in a specific embodiment, the model consists of 10 layers of a convolutional network, and there are 5 downsampling layers and 5 upper sampling layers. The process of using the model includes:

using the fundus images of the training samples as an input of a deep full convolution network, and using the corresponding manual segmentation images as an output of the deep full convolution network, to achieve hyperparameter optimization to train the deep full convolution network; and using the fundus images of the verification samples as the input of a deep full convolution network, and using the corresponding manual segmentation images as the output of the deep full convolution network, to verify the deep full convolution network.

Step 70. Selecting the deep full convolution network with the highest segmentation accuracy to segment the blood vessels of different wavebands of fundus images in the multi-spectral image includes:

performing binarization processing and center line extraction on the segmented image, traversing each point R (i, j) of the center line, the (i, j) represents horizontal and vertical positions in the image, and R represents a gray value of the point, and searching for points of 8-connected (Those are eight positively adjacent and diagonally adjacent positions on the top, bottom, left, right, top left, top right, bottom left and bottom right) neighborhoods corresponding to each point, to complete the traversing and searching for the entire blood vessels;

the emitted light intensity I represents the minimum gray value in the pixel segment of the blood vessel, and the incident light intensity $I_0$ represents the average gray value outside the pixel segment of the blood vessel, calculating the optical density value of each segment of blood vessels by the following formula:

$$OD_\lambda = lg\frac{I_0}{I} = \varepsilon_{Hbo2}C_{Hbo2}d + \varepsilon_{Hb}C_{Hb}d$$

Among then, I represents the intensity of incident light after passing through the solution, $I_0$ represents the intensity of original incident light, ε represents absorption coefficient of the solution, C represents a concentration of the solution, d represents the distance of light passing through the solution, $C_{Hbo2}$ represents absorption coefficient of oxygen and hemoglobin solution, $\varepsilon_{Hb}$ represents absorption coefficient of hemoglobin solution, $C_{Hbo2}$ represents solution concentration of oxygen and hemoglobin, and $C_{Hb}$ represents solution concentration of hemoglobin.

Step 80. calculating the blood oxygen saturation value $SO_2$ by the following formula:

$$SO_2 = a \cdot ODR + b$$

Among then, ODR represents the ratio of the optical density with unequal absorption coefficient to the optical density with equal absorption coefficient, and a and b are constant.

Step 90. monitoring the dynamic oxygen saturation value by controlling the frequency of image acquisition and outlining the region of interest.

Through the above-mentioned imaging system and method of multi-spectral fundus using dynamic visual stimulation, static multi-spectral fundus static imaging can be expanded to the field of dynamic functional imaging by combining with dynamic visual stimulation, and its combination with image processing and machine learning can help improve universality and accuracy of the diagnosis method of fundus diseases.

Finally, it should be noted that the purpose of publishing the embodiments is to help further understand the present application, but those skilled in the art can understand that various substitutions and modifications are possible without departing from the spirit and scope of the present application and its claims. Therefore, the present application should not be limited to the content disclosed in the embodiments, and the scope of protection of the present application is subject to the scope defined by its claims.

In the descriptions of this specification, the description with reference to the terms "embodiment", "embodiments", "examples", "specific examples", or "some examples" means specific features described in conjunction with the embodiments or examples, structure, material or characteristic are included in at least one embodiment or example of the present application. In this specification, the schematic expression of the above term does not necessarily refer to the same embodiment or example. Moreover, the specific features, structures, materials, or characteristics described may be combined in any one or more embodiments or examples in any suitable manner.

Although the embodiments of the present application have been shown and described, those skilled in the art may understand that various changes, modifications, replacements, and variations can be made to these embodiments without departing from the principle and purpose of the present application. The scope of the application is defined by the claims and their equivalents.

INDUSTRIAL APPLICABILITY

By applying the technical solution of the present application, the present application can capture the physiological state of the fundus before and after different optical stimulation, and detect the response of the fundus to external optical stimulation, thereby realizing dynamic multi-spectral fundus functional imaging.

What is claimed is:

1. An imaging method using a multi-spectral fundus imaging system using a dynamic visual stimulation, comprising:
   1) acquiring a multi-spectral image before applying optical stimulation:
      a) monitoring mode:
      a camera first works in an infrared light monitoring mode after upon start-up, adjusting a relative position of the multi-spectral fundus imaging system and a fundus of a subject, and adjusting a focusing of the camera to find an area of the fundus of the subject;

b) external trigger mode:

after finding the area of the fundus of the subject, the camera works in an external or internal trigger mode, and a computer controls a multi-spectral light source to synchronize with the camera; monochromatic excitation light emitted by the multi-spectral light source passes through a multi-in-one ring-shaped optical fiber bundle and is output from a ring-shaped light outlet to form a ring-shaped light; the ring-shaped light being focused and changed by a first focusing lens and light path adjustment device; and reflected around a central hole of a mid-pass mirror; the ring-shaped light entering into the fundus after being focused by a second focusing lens; reflected imaging light from the fundus is focused by the second focusing lens to the central hole of the mid-pass mirror and passes through the central hole; then passing through an imaging focusing lens group and entering the camera; the computer controls the multi-spectral light source and the camera to perform static imaging to complete a multi-spectral fundus image acquisition;

c) the multi-spectral light source changes a wavelength of the excitation light and the computer controls the multi-spectral light source to synchronize with the camera; the camera simultaneously takes corresponding multi-spectral fundus images of the corresponding wavelength, and the steps a) and b) are repeated until multi-spectral fundus images corresponding to multiple different wavelengths are taken;

d) transmitting to the computer to form a set of multi-spectral images;

2) applying optical stimulation:

a) adjusting a dichroic mirror to enter a light path; and the computer controls an optical stimulation device to send a pattern, which is reflected by the dichroic mirror, and then passes through the imaging focusing lens group, the central hole of the mid-pass mirror, and the second focusing lens in sequence, and transmits to the fundus; a contrast between light and dark in the pattern corresponds to a strength of an optical stimulation to the fundus when the dynamic visual stimulation of the fundus is regulated;

b) after the optical stimulation ends, turning off the optical stimulation device and moving the dichroic mirror out of the light path;

3) acquiring multiple sets of multi-spectral images in time series after applying optical stimulation:

according to the method in step 1), performing multi-spectral image acquisition at different time points on the fundus after optical stimulation by the camera, and transmitting it to the computer; and calculating a blood oxygen saturation value:

4) constituting functional imaging by multiple multi-spectral imaging at different time points before and after applying optical stimulation, and calculating a blood oxygen saturation value by a computer according to the multiple multi-spectral images at different time points before and after the applying of optical stimulation, and monitoring a dynamic blood oxygen saturation value to evaluate dynamic response and recovery of a fundus circulation and nervous system to optical stimulation.

2. The imaging method of the multi-spectral fundus imaging system using dynamic visual stimulation of claim 1, wherein calculating the blood oxygen saturation value and monitoring the dynamic blood oxygen saturation value in step 4) comprises:

performing preprocessing of the fundus images in multi-spectral images by the computer at different wavelengths at the same time, the preprocessing comprising image unevenness correction, light intensity correction and image denoising;

performing blood vessels segmentation on the fundus images after being preprocessed by a network model obtained by pre-training and being verified to obtain segmented images; wherein the network model is a model for the calculation of blood vessels segmentation based on deep learning algorithms;

performing binarization processing and center line extraction on one of the segmented images, traversing each point R (i, j) of the center line, and searching for points of 8-connected neighborhoods corresponding to each point, to complete the traversing and searching for all the blood vessels; wherein (i, j) represents horizontal and vertical positions in the image, and R represents a gray value of the point;

calculating an optical density value of each segment of blood vessels under a specified wavelength light based on results of the traversing and searching for the blood vessels;

calculating the blood oxygen saturation value according to the optical density value of each segment of blood vessels under the specified wavelength light; and outlining a region of interest of the fundus image by controlling an image acquisition frequency, and performing the monitoring of the dynamic blood oxygen saturation value based on the region of interest.

3. The imaging method of the multi-spectral fundus imaging system using dynamic visual stimulation of claim 2, wherein the method further comprises:

obtaining training samples and verification samples; wherein the training samples and the verification samples each comprise multiple sets of samples, and each set of samples comprises a fundus image and its corresponding manual segmentation image;

using the fundus images of the training samples as an input of a deep full convolution network, and using the corresponding manual segmentation images as the output of the deep full convolution network, to achieve hyperparameter optimization to train the deep full convolution network;

using the fundus images of the verification samples as the input of a deep full convolution network, and using the corresponding manual segmentation images as the output of the deep full convolution network, to verify the deep full convolution network; and determining the deep full convolution network with a segmentation accuracy as the network model configured for segmenting blood vessels of different wavebands of fundus images in the multi-spectral image.

4. The imaging method of the multi-spectral fundus imaging system using dynamic visual stimulation of claim 3, wherein the steps of obtaining training samples and verification samples comprise:

performing manual segmentation onto multiple fundus images at the same wavelength to obtain manual segmentation image of each fundus image;

making a set of samples according to the fundus images and its corresponding manual segmentation images based on each manual segmentation image of the fundus image obtained, and a number of the samples is larger than 100; and using a part of the samples as the training samples, and using another part of the samples as the verification samples, and a number of verification samples are greater than 20.

5. The imaging method of the multi-spectral fundus imaging system using dynamic visual stimulation of claim 2, wherein the network model is a full convolution network structure comprising at least 10 convolutional layers.

6. The imaging method of the multi-spectral fundus imaging system using dynamic visual stimulation of claim 2, wherein the steps of calculating the optical density value of each segment of blood vessels under the specified wavelength light comprise:

calculating the optical density value of each segment of blood vessels by the following formula:

$$OD_\lambda = lg\frac{I_0}{I} = \varepsilon_{Hbo2}C_{Hbo2}d + \varepsilon_{Hb}C_{Hb}d$$

wherein $OD_\lambda$ represents optional density, I represents intensity of incident light passing through a solution, $I_0$ represents an intensity of original incident light, $\varepsilon$ represents absorption coefficient of the solution, C represents a concentration of the solution, d represents a distance of light passing through the solution, $C_{Hbo2}$ represents absorption coefficient of oxygen and hemoglobin solution, $\varepsilon_{Hb}$ represents absorption coefficient of hemoglobin solution, $C_{Hbo2}$ represents solution concentration of oxygen and hemoglobin, and $C_{Hb}$ represents solution concentration of hemoglobin.

7. The imaging method of the multi-spectral fundus imaging system using dynamic visual stimulation of claim 2, wherein the steps of calculating the blood oxygen saturation value according to the optical density value of each segment of blood vessels under the specified wavelength light comprise:

calculating the blood oxygen saturation $SO_2$ by the following formula:

$$SO_2 = a \cdot ODR + b$$

wherein ODR=OD unequal absorption/OD equal absorption represents a ratio of optical density with unequal absorption coefficient to the optical density with equal absorption coefficient, and a and b are constant.

* * * * *